US012650434B2

(12) United States Patent (10) Patent No.: US 12,650,434 B2
Colombel et al. (45) Date of Patent: Jun. 9, 2026

(54) METHODS OF MONITORING INFLAMMATORY BOWEL DISEASES

(71) Applicant: ICAHN SCHOOL OF MEDICINE AT MOUNT SINAI, New York, NY (US)

(72) Inventors: Jean-Frederic Colombel, New York, NY (US); James Ferrara, New York, NY (US); John E. Levine, New York, NY (US); Umut Ozbek, New York, NY (US); Ryan Ungaro, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 441 days.

(21) Appl. No.: 18/266,497

(22) PCT Filed: Dec. 10, 2021

(86) PCT No.: PCT/US2021/062764
§ 371 (c)(1),
(2) Date: Jun. 9, 2023

(87) PCT Pub. No.: WO2022/125867
PCT Pub. Date: Jun. 16, 2022

(65) Prior Publication Data
US 2024/0044916 A1 Feb. 8, 2024

Related U.S. Application Data

(60) Provisional application No. 63/124,410, filed on Dec. 11, 2020.

(51) Int. Cl.
| | |
|---|---|
| *G01N 33/53* | (2006.01) |
| *A61K 31/4985* | (2006.01) |
| *A61K 31/519* | (2006.01) |
| *A61K 31/52* | (2006.01) |
| *A61K 31/573* | (2006.01) |
| *A61K 31/606* | (2006.01) |
| *A61K 31/655* | (2006.01) |
| *A61K 39/395* | (2006.01) |
| *G01N 33/68* | (2006.01) |

(52) U.S. Cl.
CPC ..... *G01N 33/6893* (2013.01); *A61K 31/4985* (2013.01); *A61K 31/519* (2013.01); *A61K 31/52* (2013.01); *A61K 31/573* (2013.01);

*A61K 31/606* (2013.01); *A61K 31/655* (2013.01); *A61K 39/3955* (2013.01); *G01N 2800/065* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2011/0212104 A1 | 9/2011 | Beaumont et al. | |
| 2015/0072879 A1 | 3/2015 | Pricen et al. | |
| 2016/0312302 A1 | 10/2016 | Clarke et al. | |
| 2018/0010198 A1 | 1/2018 | Anjamshoaa et al. | |
| 2019/0259467 A1 | 8/2019 | Ferrara et al. | |
| 2020/0237801 A1* | 7/2020 | Bellinvia | A61K 31/7125 |
| 2020/0264171 A1 | 8/2020 | Jain et al. | |
| 2020/0323893 A1 | 10/2020 | Shea et al. | |

OTHER PUBLICATIONS

Marafini et al., Serum regenerating islet-derived 3-alpha is a biomarker of mucosal enteropathies, Aliment Pharmacol Ther, 2014, 40: pp. 974-981. (Year: 2014).*
ASGE Guideline, The role of endoscopy in inflammatory bowel disease, vol. 81, No. 5, 2015, pp. 1101-1121e13. (Year: 2015).*
International Search Report and Written Opinion Issued in PCT/US2021/062764 dated Apr. 1, 2022.
Tsuchida et al., "Expression of REG family genese in human inflammatory bowel diseases and its regulation", Biochemistry and Biophysics Reports, 2017, vol. 12, pp. 198-205.
D'Haens et al., "Development and Validation of a Test to Monitor Endoscopic Activity in Patients With Crohn's Disease Based on Serum Levels of Proteins", Gastroenterology, 2020, vol. 158, pp. 515-523.
Van Beelen Granlund et al., "REG gene expression in inflamed and healthy colon mucosa explored by in situ hybridisation", Cell Tissue Res, 2013, vol. 352, pp. 639-646.
Hajian-Tilaki, "Receiver Operating Characteristic (ROC) Curve Analysis for Medical Diagnostic Test Evaluation", 5 Caspian J. Intern Med, 2013, vol. 4, No. 2, pp. 627-635.

* cited by examiner

*Primary Examiner* — Gary Counts
(74) *Attorney, Agent, or Firm* — Lathrop GPM LLP; Malaika O.D. Tyson

(57) ABSTRACT

The present application discloses diagnostic methods and kits for detecting disease activity in a subject having an inflammatory bowel disease, such as Crohn's disease. Methods of treating endoscopically active gastrointestinal disease, as well as methods of determining effectiveness of a treatment for endoscopically active gastrointestinal disease in a subject, are also disclosed.

17 Claims, 6 Drawing Sheets

METHODS OF MONITORING INFLAMMATORY BOWEL DISEASES

CROSS-REFERENCE TO RELATED APPLICATIONS

This patent application is a U.S. National Phase of International Patent Application No. PCT/US2021/062764, filed on Dec. 10, 2021, which claims priority to U.S. Provisional Application No. 63/124,410, filed Dec. 11, 2020. The entire contents of these applications are incorporated herein by reference in their entirety.

FIELD OF THE INVENTION

The present application relates to methods and kits for detecting disease activity in inflammatory bowel diseases, such as Crohn's disease.

BACKGROUND

Treatment strategies for inflammatory bowel diseases (IBDs), such as Crohn's disease (CD), have evolved to incorporate a treat to target (T2T) approach in which symptoms alone are not sufficient but achieving the target of objective healing of the intestine is the preferred treatment endpoint. Healing of the intestine (endoscopic healing) is determined through invasive colonoscopy tests in which endoscopic scoring (using the SES-CD score) is used to decide if a patient is in remission or not. Non-invasive blood markers of endoscopic healing are limited and currently are limited to C-reactive protein (CRP). A stool biomarker of inflammation, fecal calprotectin, is also available and can offer better diagnostic accuracy but can create more logistical challenges and patients are often less likely to complete. Accordingly, there is an unmet need in the art for improved non-invasive diagnostics to monitor disease activity in inflammatory bowel diseases.

SUMMARY OF THE INVENTION

In one aspect, provided herein is a method for detecting endoscopically active gastrointestinal disease in a subject having an inflammatory bowel disease, said method comprising:

detecting, in a biological sample from the subject, expression level of regenerating islet-derived protein 3 alpha (REG3α); and applying a statistical algorithm to said expression level to generate a REG3α index score to detect presence or absence of endoscopically active gastrointestinal disease in the subject.

In some embodiments, the method further comprises:

determining that the subject (i) is having, or likely to have, endoscopically active gastrointestinal disease when the REG3α index score is higher than an optimal classification threshold or (ii) is, or likely to be, in endoscopic remission when the REG3α index score is lower than or equal to the optimal classification threshold.

In one embodiment, the statistical algorithm is $\log[p/(1-p)]=-1.949+1.172(\log_{10} REG3\alpha)$ and the REG3α index score is the probability (p) obtained from said statistical algorithm.

In one embodiment, the optimal classification threshold is about 0.43.

In some embodiments, the detecting step further comprises detecting the expression level of C-reactive protein (CRP), and the method comprises applying a statistical algorithm to said expression levels of REG3α and CRP to generate a combined REG3α/CRP index score.

In some embodiments, the method further comprises:

determining that the subject (i) is having, or likely to have, endoscopically active gastrointestinal disease when the combined REG3α/CRP index score is higher than an optimal classification threshold or (ii) is, or likely to be, in endoscopic remission when the combined REG3α/CRP index score is lower than or equal to the optimal classification threshold.

In one embodiment, the statistical algorithm is $\log[p/(1-p)]=-2.140+1.045(\log_{10} REG3\alpha)+0.667(\log_{10} CRP)$ and the combined REG3α/CRP index score is the probability (p) obtained from said statistical algorithm.

In some embodiments, the optimal classification threshold is selected from 0.35, 0.36, 0.37, 0.38, 0.39, 0.40, 0.41, 0.42, 0.43 and 0.44. In one embodiment, the optimal classification threshold is about 0.39.

In various embodiments, the subject is a mammal. In some embodiments, the subject is a human.

In various embodiments, the inflammatory bowel disease is Crohn's disease, colitis, ulcerative colitis, ileocolitis, ileitis, gastroduodenal Crohn's disease, jejunoileitis, or Crohn's colitis. In some embodiments, the inflammatory bowel disease is Crohn's disease.

In some embodiments, the subject is treatment naïve for inflammatory bowel disease. In some embodiments, the subject is undergoing treatment for inflammatory bowel disease. In some embodiments, the subject has undergone therapeutic treatment for inflammatory bowel disease. In some embodiments, the subject is undergoing or has undergone treatment with a therapeutic agent selected from Adalimumab (HUMIRA®), Adalimumab-adbm (CYLTEZO®), Adalimumab-atto (AMJEVITA®), Certolizumab (CIMZIA®), Infliximab (REMICADE®), Infliximab-abda (RENFLEXIS®), Infliximab-dyyb (INFLECTRA®), Ustekinumab (STELARA®), Vedolizumab (ENTYVIO®), upadacitinib, tofacitinib, Receptos, mesalamine, sulfasalazine, prednisone, azathioprine, mercaptopurine, and methotrexate, or any combination thereof. In some embodiments, the subject has undergone surgical resection as a treatment for inflammatory bowel disease.

In various embodiments, the biological sample is whole blood, plasma, serum, urine, saliva, sputum, bronchial lavage fluid, tears, or stool. In some embodiments, the biological sample is a biofluid sample. In one embodiment, the biological sample is serum.

In various embodiments, the detecting step comprises: contacting the biological sample with a binding partner for REG3α or CRP, and detecting binding between REG3α or CRP and its binding partner. In some embodiments the binding partner is an antibody. In some embodiments, detecting binding between REG3α and its binding partner is carried out using an enzyme-linked immunosorbent assay (ELISA), a collaborative enzyme enhanced reactive immunoassay (CEER), a homogenous mobility shift assay (HMSA), an immunohistochemical assay, fluorescence activated cell sorting (FACS), or a Western blot.

In some embodiments, the statistical algorithm comprises a model relating the expression levels of REG3α or REG3α/CRP to a Simple Endoscopic Score for Crohn's Disease (SES-CD), Crohn's Disease Endoscopic Index of Severity (CDEIS), fecal calprotectin score and/or MonitR test. In some embodiments, the model is derived by using logistic regression to model diagnostic specificity.

In another aspect, provided herein is a method of treating endoscopically active gastrointestinal disease in a subject, said method comprising:

selecting a subject having a REG3α or a combined REG3α/CRP index score indicating the presence of endoscopically active gastrointestinal disease in the subject and administering to the selected subject a therapeutic agent under conditions effective to treat the endoscopically active gastrointestinal disease in the subject.

In some embodiments, the presence of endoscopically active gastrointestinal disease is determined according to the diagnostic methods described herein.

In various embodiments, the subject is a mammalian subject. In some embodiments, the subject is a human.

In various embodiments, the subject has an inflammatory bowel disease which is Crohn's disease, colitis, ulcerative colitis, ileocolitis, ileitis, gastroduodenal Crohn's disease, jejunoileitis, or Crohn's colitis. In some embodiments, the subject has Crohn's disease.

In some embodiments, the subject is treatment naïve for inflammatory bowel disease. In some embodiments, the subject has undergone prior treatment with a therapeutic agent for inflammatory bowel disease. In some embodiments, the subject has undergone surgical resection as a treatment for inflammatory bowel disease. In some embodiments, the therapeutic agent is one or more of Adalimumab (HUMIRA®), Adalimumab-adbm (CYLTEZO®), Adalimumab-atto (AMJEVITA®), Certolizumab (CIMZIA®), Infliximab (REMICADE®), Infliximab-abda (RENFLEXIS®), Infliximab-dyyb (INFLECTRA®), Ustekinumab (STELARA®), Vedolizumab (ENTYVIO®), upadacitinib, tofacitinib, Receptos, mesalamine, sulfasalazine, prednisone, azathioprine, mercaptopurine, and methotrexate, or any combination thereof.

In another aspect, provided herein is a method of determining effectiveness of a treatment for endoscopically active gastrointestinal disease in a subject, said method comprising:

detecting an expression level of regenerating islet-derived protein 3 alpha (REG3α) or REG3α/C-reactive protein (CRP) in a first biological sample from a subject before the subject is treated for endoscopically active gastrointestinal disease;

detecting an expression level of REG3α or REG3α/CRP in a second biological sample from the subject after the subject has received a treatment for the endoscopically active gastrointestinal disease; and comparing the expression level of REG3α or REG3α/CRP in the second biological sample to the expression level of REG3α or REG3α/CRP in the first biological sample to determine effectiveness of the treatment in the subject.

In some embodiments, the method further comprises:

applying a statistical algorithm to the expression level of REG3α or REG3α/CRP in the first and second biological samples to produce an index score for endoscopically active gastrointestinal disease in the subject prior to the comparing step.

In some embodiments, the comparing step is carried out by determining whether the index score for endoscopically active gastrointestinal disease in the first biological sample is different than the index score for endoscopically active gastrointestinal disease in the second biological sample.

In some embodiments, the treatment is (1) effective when the index score for endoscopically active gastrointestinal disease in the first biological sample is higher than the index score for endoscopically active gastrointestinal disease in the second biological sample; and (2) not effective when the index score for endoscopically active gastrointestinal disease in the first biological sample is lower than or equal to the index score for endoscopically active gastrointestinal disease in the second biological sample.

In various embodiments, the subject is a human subject. In various embodiments, the subject has an inflammatory bowel disease which is Crohn's disease, colitis, ulcerative colitis, ileocolitis, ileitis, gastroduodenal Crohn's disease, jejunoileitis, or Crohn's colitis. In some embodiments, the subject has Crohn's disease.

In various embodiments, the biological sample is whole blood, plasma, serum, urine, saliva, sputum, bronchial lavage fluid, tears, or stool. In some embodiments, the biological sample is a biofluid sample.

In some embodiments, the treatment comprises administering a therapeutic agent selected from Adalimumab (HUMIRA®), Adalimumab-adbm (CYLTEZO®), Adalimumab-atto (AMJEVITA®), Certolizumab (CIMZIA®), Infliximab (REMICADE®), Infliximab-abda (RENFLEXIS®), Infliximab-dyyb (INFLECTRA®), Ustekinumab (STELARA®), Vedolizumab (ENTYVIO®), upadacitinib, tofacitinib, Receptos, mesalamine, sulfasalazine, prednisone, azathioprine, mercaptopurine, and methotrexate, and any combination thereof.

BRIEF DESCRIPTION OF THE DRAWINGS

The accompanying Figures, which are incorporated in and constitute a part of this specification, illustrate several aspects described below.

DETAILED DESCRIPTION

Figure 1:
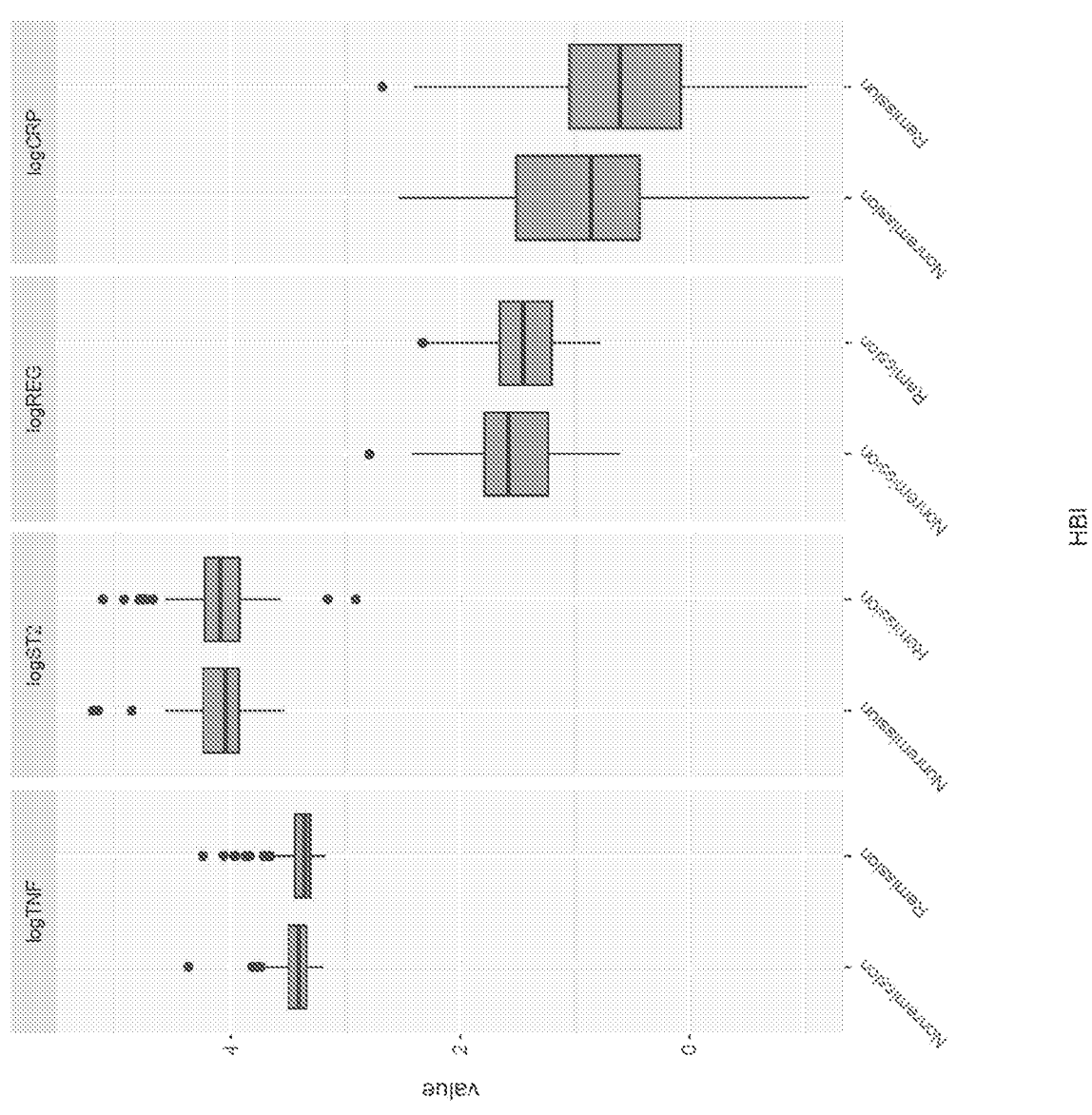
FIG. 1 is a graph showing boxplots of log-transformed serum biomarker concentrations (tumor necrosis factor (TNF), interleukin-1 receptor-like-1 protein (IL1RL1 or ST2), regenerating islet-derived protein 3 alpha (REG3α) and C-reactive protein (CRP)) in patients under clinical remission vs non-remission as defined by the Harvey Bradshaw Index (HBI). P-values between the HBI groups: p-value (log TNF)=0.010; p-value (log ST2)=0.728; p-value (log REG3α)=0.026; p-value (log CRP)=0.004.

The present application provides, among other things, methods and kits for non-invasive detection of disease activity in inflammatory bowel disease patients. This application is based on a surprising and unexpected discovery that the biomarker REG3α is a highly sensitive measure for healing of the intestine in patients with Crohn's disease. In some embodiments, REG3α can be used in combination with the biomarker, C-reactive protein (CRP), in the methods described herein. These methods can serve as a non-invasive approach to monitor patients and avoid more frequent invasive colonoscopies and allow for adjustment of medical therapy.

Definitions

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or examples. The invention is capable of other embodiments and of being practiced or carried out in various ways. Also, in describing the exemplary embodiments, specific terminology will be resorted to for the sake of clarity.

The term "inflammatory bowel disease" or "IBD" refers to a heterogeneous group of chronic inflammatory disorders of the gastrointestinal tract that includes Crohn's disease (CD) and ulcerative colitis (UC). Other diseases contemplated for diagnostics or treatment using the methods of the present disclosure include colitis, ileocolitis, ileitis, gastroduodenal CD, jejunoileitis, and Crohn's colitis. All of these diseases fall within the scope of the term "inflammatory bowel disease" as used in this application. In some embodiments, the inflammatory bowel disease is Crohn's disease (CD). In some embodiments, the inflammatory bowel disease is ulcerative colitis (UC).

The term "endoscopically active gastrointestinal disease" as used herein with reference to inflammatory bowel disease subjects, means there is active inflammation in the gastrointestinal tract during a scope (e.g., a colonoscopy or a sigmoidoscopy). The endoscopically active gastrointestinal disease may have a mild, moderate or severe disease activity. In some embodiments, an endoscopically active gastrointestinal disease can be defined using an endoscopic score of disease activity. For example, for Crohn's disease, an endoscopically active gastrointestinal disease refers to a Simple Endoscopic Score for Crohn's Disease (SES-CD) of greater than 3 (Daperno M. et al. Gastrointest Endosc. 2004; 60: 505-512, which is incorporated herein by reference in its entirety).

The term "endoscopic remission" as used herein with reference to inflammatory bowel disease subjects, means there is no or minimal inflammation in the gastrointestinal tract during a scope (e.g., a colonoscopy or a sigmoidoscopy). In some embodiments, endoscopic remission can be defined using an endoscopic score of disease activity. For example, for Crohn's disease, an endoscopic remission refers to a SES-CD of less than or equal to 3 (Daperno M.

et al. Gastrointest Endosc. 2004; 60: 505-512, which is incorporated herein by reference in its entirety).

The term "REG3α" as used herein refers to a "regenerating islet-derived protein 3 alpha" or its nucleic acid (e.g., mRNA).

The term "CRP" as used herein refers to a "C-reactive protein" or its nucleic acid (e.g., mRNA).

The term "index score" as used herein with reference to the biomarker(s) refers to an empirically derived index that is derived based on an analysis of relevant biomarker(s). In some embodiments, the measured levels of the biomarker(s) are transformed into the index score by a statistical algorithm. In some embodiments, the index score is a synthetic or human derived output, score, or cut off value(s), which express the biological data in numerical terms. The index can be used to determine or make or aid in making a clinical decision. An index score can be measured multiple instances over the course of time. In one embodiment, the algorithm can be trained with known samples and thereafter validated with samples of known identity. In some embodiments, the index score is probability (p) obtained from a statistical algorithm described herein.

The term "biological sample" as used herein includes any biological specimen obtained from a subject or patient. Biological samples that can be used in the methods of the present disclosure include, without limitation, whole blood, plasma, serum, red blood cells, white blood cells (e.g., peripheral blood mononuclear cells (PBMC), polymorphonuclear (PMN) cells), ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by random periareolar fine needle aspiration), any other bodily fluid, a tissue sample such as a biopsy of a site of inflammation (e.g., needle biopsy), and cellular extracts thereof. In some embodiments, the biological sample is a biofluid sample. In some embodiments, the biological sample is serum.

The terms "marker" and "biomarker" are used herein interchangeably to refer to any biochemical markers, serological markers, protein markers, genetic markers, analytes, and/or other clinical or echographic characteristics, that can be measured in a sample. In certain embodiments, a marker can be used to detect endoscopically active gastrointestinal disease in a sample from an individual with a disease such as inflammatory bowel disease including Crohn's disease and ulcerative colitis.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms "a," "an," and "the" do not denote a limitation of quantity, but rather denote the presence of "at least one" of the referenced item.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

Throughout this description, various components may be identified having specific values or parameters, however, these items are provided as exemplary embodiments. Indeed, the exemplary embodiments do not limit the various aspects and concepts of the present invention as many comparable parameters, sizes, ranges, and/or values may be implemented. The terms "first," "second," and the like, "primary," "secondary," and the like, do not denote any order, quantity, or importance, but rather are used to distinguish one element from another.

As used herein, the term "and/or" may mean "and," it may mean "or," it may mean "exclusive-or," it may mean "one," it may mean "some, but not all," it may mean "neither," and/or it may mean "both." The term "or" is intended to mean an inclusive "or."

It is noted that terms like "specifically," "preferably," "typically," "generally," and "often" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention. It is also noted that terms like "substantially" and "about" are utilized herein to represent the inherent degree of uncertainty that may be attributed to any quantitative comparison, value, measurement, or other representation.

References to "one embodiment," "an embodiment," "example embodiment," "some embodiments," "certain embodiments," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

The dimensions and values disclosed herein are not to be understood as being strictly limited to the exact numerical values recited. Instead, unless otherwise specified, each such dimension is intended to mean both the recited value and a functionally equivalent range surrounding that value. For example, a value disclosed as "0.5" is intended to mean "about 0.5."

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described hereinafter as making up the various elements of the present invention are intended to be illustrative and not restrictive. Many suitable materials that would perform the same or a similar function as the materials described herein are intended to be embraced within the scope of the invention. Such other materials not described herein can include, but are not limited to, materials that are developed after the time of the development of the invention, for example. Any dimensions listed in the various drawings are for illustrative purposes only and are not intended to be limiting. Other dimensions and proportions are contemplated and intended to be included within the scope of the invention.

As used herein, the term "subject" or "patient" refers to mammals and includes, without limitation, human and veterinary animals. In a preferred embodiment, the subject is human.

The terms "treat" or "treatment" of a state, disorder or condition include: (1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

A prognosis may be any assessment of the risk of disease outcome in an individual in which a particular disease has been diagnosed. Assessing the risk further encompasses prediction of therapeutic response in which a treatment regimen is chosen based on the assessment. Assessing the risk also encompasses a prediction of overall survival after diagnosis.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. 1985); Transcription and Translation (B. D. Hames & S. J. Higgins, eds. 1984); Animal Cell Culture (R. I. Freshney, ed. 1986); Immobilized Cells and Enzymes (IRL Press, 1986; B. Perbal, A Practical Guide To Molecular Cloning. 1984; F. M. Ausubel et al. (eds.), Current Protocols in Molecular Biology, John Wiley & Sons, Inc. 1994); among others.

Diagnostic Methods of the Invention

In some aspects, provided herein are methods for detecting endoscopically active gastrointestinal disease in a subject having an inflammatory bowel disease.

In one aspect, provided herein is a method for detecting endoscopically active gastrointestinal disease in a subject having an inflammatory bowel disease, the method comprising:

detecting, in a biological sample from a subject, expression level of regenerating islet-derived protein 3 alpha (REG3α); and applying a statistical algorithm to said expression level to generate a REG3α index score to detect presence or absence of endoscopically active gastrointestinal disease in the subject.

In some embodiments, the method further comprises comparing the REG3α index score to an optimal classification threshold.

In some embodiments of the methods described herein, the method comprises determining that the subject (i) is having, or likely to have, endoscopically active gastrointestinal disease when the REG3α index score is higher than an optimal classification threshold or (ii) is, or likely to be, in endoscopic remission when the REG3α index score is lower than or equal to the optimal classification threshold.

In some embodiments, the statistical algorithm is $\log[p/(1-p)]=-1.949+1.172(\log_{10}$ REG3α) and the REG3α index score is the probability (p) obtained from the statistical algorithm.

In some embodiments, the scale of the REG3α index score is from 0-1. In some embodiments, the optimal classification threshold is selected from a value between 0-1. In some embodiments, the optimal classification threshold is selected from a value between 0.3-0.5. In some embodiments, the optimal classification threshold is selected from 0.38, 0.39, 0.40, 0.41, 0.42, 0.43, 0.44, 0.45, 0.46, 0.47, and 0.48. In one embodiment, the optimal classification threshold is 0.38. In one embodiment, the optimal classification threshold is 0.39. In one embodiment, the optimal classification threshold is 0.40. In one embodiment, the optimal classification threshold is 0.41. In one embodiment, the optimal classification threshold is 0.42. In one embodiment, the optimal classification threshold is 0.43. In one embodiment, the optimal classification threshold is 0.44. In one embodiment, the optimal classification threshold is 0.45. In one embodiment, the optimal classification threshold is 0.46. In one embodiment, the optimal classification threshold is 0.47. In one embodiment, the optimal classification threshold is 0.48. For an exemplary study cohort, the test sensitivity and specificity associated with the optimal classification threshold of 0.43 is 0.76 and 0.55, respectively.

In some embodiments of the methods described herein, the method further comprises detecting the expression level of C-reactive protein (CRP). In such embodiments, the method comprises applying a statistical algorithm to the expression levels of REG3α and CRP to generate a combined REG3α/CRP index score. In some embodiments, the method further comprises comparing the combined REG3α/CRP index score to an optimal classification threshold.

In some embodiments of the methods described herein, the method comprises determining that the subject (i) is having, or likely to have, endoscopically active gastrointestinal disease when the combined REG3α/CRP index score is higher than an optimal classification threshold or (ii) is, or likely to be, in endoscopic remission when the combined REG3α/CRP index score is lower than or equal to the optimal classification threshold.

In some embodiments, the statistical algorithm is $\log[p/(1-p)]=-2.140+1.045(\log_{10}$ REG3α)$+0.667(\log_{10}$ CRP) and the combined REG3α/CRP index score is the probability (p) obtained from the statistical algorithm.

In some embodiments, the scale of the combined REG3α/CRP index score is from 0-1. In some embodiments, the optimal classification threshold is selected from a value between 0-1. In some embodiments, the optimal classification threshold is selected from a value between 0.3-0.5. In some embodiments, the optimal classification threshold is selected from 0.35, 0.36, 0.38, 0.39, 0.40, 0.41, 0.42, 0.43 and 0.44. In one embodiment, the optimal classification threshold is 0.35. In one embodiment, the optimal classification threshold is 0.36. In one embodiment, the optimal classification threshold is 0.37. In one embodiment, the optimal classification threshold is 0.38. In one embodiment, the optimal classification threshold is 0.39. In one embodiment, the optimal classification threshold is 0.40. In one embodiment, the optimal classification threshold is 0.41. In one embodiment, the optimal classification threshold is 0.42. In one embodiment, the optimal classification threshold is 0.43. In one embodiment, the optimal classification threshold is 0.44. For an exemplary study cohort, the test sensitivity and specificity associated with each of the thresholds is provided in Table 3.

Optimal classification threshold can be adjusted based on the clinical intervention and the patient population that investigators have. For some studies, based on the risk level of the intervention, for example, sensitivity is more important and the investigator may want to maximize sensitivity rather than specificity or vice versa. Therefore, the threshold after applying a statistical algorithm described herein can be different than those described above. Likewise, because patient populations may behave differently, the threshold can be adjusted accordingly for different studies even though the same statistical algorithm is applied.

In some embodiments of the methods described herein, the method further comprises detecting the expression level of one or more additional biomarkers associated with biological pathways important for promoting endoscopic healing in IBD patients. In some embodiments, the one or more additional biomarkers are selected from ANG1, ANG2, CRP, SAA1, IL7, EMMPRIN, MMP1, MMP2, MMP3, MMP9, TGFA, CEACAM1, and VCAM1, or a combination thereof. The biomarkers may be detected using methods and techniques described herein or those known in the art, for example, in U.S. Patent Publication No. US20200264171A1 and D'Haens G et al. Gastroenterology 2020; 158:515-526, both of which are incorporated herein by reference in their entirety for all purposes.

In some embodiments where one or more additional biomarkers are detected in addition to REG3α and optionally CRP, the method comprises applying a statistical algorithm to the expression levels of all detected biomarkers to generate an integrated index score. In some embodiments, the method further comprises comparing the integrated index score to an optimal classification threshold. In some embodiments, the method comprises determining that the subject (i) is having, or likely to have, endoscopically active gastrointestinal disease when the integrated index score is higher an optimal classification threshold or (ii) is, or likely to be, in endoscopic remission when the integrated index score is lower than or equal to than the optimal classification threshold.

In some embodiments, the statistical algorithm used in the methods of the present disclosure comprises one or more models relating the expression levels of at least one of the markers described herein (e.g., REG3α, CRP) to an endoscopic scoring index. In some embodiments, the endoscopic scoring index is a Simple Endoscopic Score for Crohn's Disease (SES-CD), Crohn's Disease Endoscopic Index of Severity (CDEIS), fecal calprotectin score and/or MonitR test.

CDEIS and SES-CD are each generally accepted endoscopic scoring indices conventionally used as standards to assess the state of mucosal disease in Crohn's disease patients, score mucosal status, and determine the outcome of clinical trials that utilize mucosal healing as an endpoint. In some embodiments, the equations of the statistical algorithm relate the measured biomarker expression levels of a patient to the predicted CDEIS of the patient. In some embodiments, the equations relate the measured biomarker expression levels of a patient to the predicted SES-CD of the patent. In some embodiments, a CDEIS value is converted to an SES-CD value. In some embodiments, an SES-CD value is converted to a CDEIS value. Although a linear offset between CDEIS and SES-CD is widely accepted, the disclosed methods can use a variety of statistical processes for converting scores of one index to another.

In some embodiments, the statistical algorithm includes one or more equations relating measured expression levels of the biomarker(s) to an endoscopic scoring index. The statistical algorithm can include, for example, two or more equations, three or more equations, four or more equations, five or more equations, six or more equations, seven or more equations, eight or more equations, nine or more equations, or ten or more equations. The equations can relate to raw data of biomarker expression levels, or to transformed data of the expression levels. In some embodiments, the equations relate to the natural logarithms of the biomarker expression levels.

The relationships between the biomarker expression levels and the endoscopic scoring index, biomarker index scores described herein and diagnostic prediction can be derived by any of a number of statistical processes or statistical analysis techniques. In some embodiments, logistic regression is used to derive one or more equations of the statistical algorithm. In some embodiments, linear regression is used to derive one or more equations of the algorithm. In some embodiments, ordinary least squares regression or unconditional logistic regression is used to derive one or more equations of the algorithm.

In some embodiments, the model(s) is derived by using logistic regression to model diagnostic specificity.

In one embodiment, the statistical algorithm used to relating the expression level of REG3α to SES-CD is: SES-CD~$1.172(\log_{10}$ REG3α).

In one embodiment, the statistical algorithm used to relating the expression levels of REG3α and CRP to SES-CD is: SES-CD~$1.045*\log_{10}$ REG3α+$0.667*\log_{10}$ CRP.

In some embodiments of the above methods, the subject has an inflammatory bowel disease selected from the group consisting of Crohn's disease, colitis, ulcerative colitis, ileocolitis, ileitis, gastroduodenal Crohn's disease, jejunoileitis, and Crohn's colitis. In some embodiments, the subject has Crohn's disease. In some embodiments, the subject has ulcerative colitis.

In some embodiments, the subject exhibits signs and/or symptoms for the inflammatory bowel disease. In some embodiments, the subject does not exhibit signs and/or symptoms for the inflammatory bowel disease.

Crohn's disease can be characterized by inflammation and ulceration occurring deep in the intestinal wall layers. The lower part of the small intestine, the ileum, is one of the most common areas affected. In some cases, the disease can also affect any portion of the gastrointestinal tract. Symptoms can include abdominal pain, frequently localized in the lower right side, diarrhea, and weight loss, as well as rectal bleeding and fever. The most common complication of Crohn's disease is intestinal blockage or stricture. This occurs as a result of the disease's thickening of the intestinal walls. Fistulas, which frequently occur around the anus and rectum, are another common complication of the disease. They are abnormal openings that result when ulcers in the intestine create passageways into the surrounding tissues of the bladder, vagina, or the skin.

Ulcerative colitis typically affects the colon and typically gives rise to diarrhea, abdominal cramps, and rectal bleeding, but it may also be accompanied by fatigue, weight loss, appetite loss, loss of body fluids and nutrients, and abdominal pain. A salient feature of UC is that the inflammation of the colon is uniform and continuous. The disease may be limited to the rectum (known as proctitis), may involve part of the colon, or may even involve the entire colon. The surface mucosal cells, including the submucosa and the crypt epithelium, play a role in the inflammatory reaction. As it progresses, epithelial damage ensues along with loss of surface epithelial cells. This give rise to multiple ulcerations. Accordingly, about 85% of UC patients have mild to moderate disease which can be managed without hospitalization. In the remaining 15%, the patients' entire colon are involved and the disease is accompanied by severe bloody diarrhea and systemic symptoms. Toxic dilation of the colon is common among patients with severe UC.

In some embodiments, the disclosed methods can be used to assess endoscopic healing at colonic, ileocolonic, and/or ileal disease locations in the subject.

In some embodiments, the subject is treatment naïve for inflammatory bowel disease. In some embodiments, the subject is undergoing treatment for inflammatory bowel disease. In some embodiments, the subject has undergone therapeutic treatment for inflammatory bowel disease.

In some embodiments, the subject is undergoing or has undergone treatment with a therapeutic agent selected from the group consisting of Adalimumab (HUMIRA®), Adalimumab-adbm (CYLTEZO®), Adalimumab-atto (AMJEVITA®), Certolizumab (CIMZIA®), Infliximab (REMICADE®), Infliximab-abda (RENFLEXIS®), Infliximab-dyyb (INFLECTRA®), Natalizumab (TYSABRI®), Ustekinumab (STELARA®), Vedolizumab (ENTYVIO®), upadacitinib, tofacitinib, Receptos, mesalamine, sulfasalazine, prednisone, azathioprine, mercaptopurine, and methotrexate.

In some embodiments, the subject has undergone surgical resection as a treatment for inflammatory bowel disease. In some embodiments, the disclosed methods can be used to assess endoscopic healing in the subject after surgery, such as by identifying post-operative, endoscopic recurrence in the subject.

In some embodiments, prior to the detecting step, the method further comprises obtaining a biological sample from the subject. In some embodiments, the biological sample is whole blood, plasma, serum, urine, saliva, sputum, bronchial lavage fluid, tears, or stool. In some embodiments, the biological sample is a biofluid sample (e.g., whole blood, plasma, serum, saliva, or urine). In some embodiments, the biological sample is serum.

In some embodiments of the above methods, the detecting step comprises determining the levels of REG3α and optionally CRP. In further embodiments, the detecting step comprises determining the levels of one and more additional markers disclosed herein (e.g., ANG1, ANG2, CRP, SAA1, IL7, EMMPRIN, MMP1, MMP2, MMP3, MMP9, TGFA, CEACAM1, and/or VCAM1). In some embodiments, the levels of at least one of the markers disclosed herein that are measured are expression levels of these markers.

In some embodiments, detecting expression levels of at least one of the markers disclosed herein (e.g., REG3$\alpha$, CRP) involves contacting the biological sample with a binding partner for the marker, and detecting binding between the marker (e.g., REG3$\alpha$, CRP) and its binding partner. In some embodiments, the binding partner is an antibody. In some embodiments, the binding between the marker (e.g., REG3$\alpha$, CRP) and its binding partner is detected using an enzyme-linked immunosorbent assay (ELISA), a collaborative enzyme enhanced reactive immunoassay (CEER), a homogenous mobility shift assay (HMSA), an immunohistochemical assay, fluorescence activated cell sorting (FACS), or a Western blot. ELISA may be carried out using commercially available kits for determining the presence or level of a biomarker in a serum, plasma, saliva, or urine sample from, e.g., MBL International Corp. (Woburn, MA), Antigenix America Inc. (Huntington Station, NY), Promega (Madison, WI), R&D Systems, Inc. (Minneapolis, MI), Invitrogen (Camarillo, CA), CHEMICON International, Inc. (Temecula, CA), Neogen Corp. (Lexington, KY), PeproTech (Rocky Hill, NJ), Alpco Diagnostics (Salem, NH), Pierce Biotechnology, Inc. (Rockford, IL), and/or Abazyme (Needham, MA). CEER may be carried out as described in art, e.g., in International Patent Application Publication NOs. WO 2008/036802, WO 2009/012140, WO 2009/108637, WO 2010/132723, WO 2011/008990, WO 2011/050069, WO 2012/088337, WO 2012/119113, and WO 2013/033623, each of which are herein incorporated by reference in their entirety for all purposes.

In some embodiments, the expression levels of at least one of the markers disclosed herein (e.g., REG3$\alpha$, CRP) are measured in terms of mRNA expression with an assay such as, for example, a hybridization assay or an amplification-based assay.

In some embodiments, the determination of the levels of at least one of the markers disclosed herein (e.g., REG3$\alpha$, CRP) further comprises isolating nucleic acid and/or protein from the sample. In some embodiments, the marker(s) is detected directly. In some of these embodiments, the marker detection comprises a method such as, for example and not limitation, Sanger sequencing, pyrosequencing, SOLID sequencing, massively parallel sequencing, barcoded DNA sequencing, PCR, real-time PCR, quantitative PCR, microarray analysis of the isolated nucleic acid with a gene chip, restriction fragment length polymorphism analysis, allele specific ligation, and comparative genomic hybridization. In other embodiments, the marker(s) is detected indirectly. In some of these embodiments, the marker detection comprises a method such as, for example and not limitation, microarray/microchip analysis of the isolated nucleic acid, DNA/RNA in situ hybridization, RNase protection assay, Northern blot, reverse transcriptase PCR, quantitative PCR, quantitative reverse transcriptase PCR, quantitative real-time reverse transcriptase PCR, reverse transcriptase treatment followed by direct sequencing, flow cytometry, bead-based flow-cytometry, immunohistochemistry, ELISA, MA, Western blot, immunoaffinity chromatography, HPLC, mass spectrometry, mass spectroscopy, protein microarray/microchip analysis, PAGE analysis, isoelectric focusing, immunoturbidimetry, rapid immunodiffusion, laser nephelometry, visual agglutination, quantitative Western blot analysis, multiple reaction monitoring-mass spectrometry (MRM Proteomics), Lowry assay, Bradford assay, BCA assay, UV spectroscopic assays, and 2-D gel electrophoresis.

In some embodiments of the above methods, the steps of applying a statistical algorithm to generate an index score, comparing an index score to an optimal classification threshold, and/or determining disease activity in the subject may be performed by a computer, as described further herein. In some embodiments, it may be convenient to prepare a report of results of the patient's diagnosis. Thus, some embodiments of the methods of the disclosure comprise a further step of preparing a report containing results from the diagnosis, wherein said report is written in a computer readable medium, printed on paper, or displayed on a visual display. In certain embodiments, it may be convenient to report diagnostic results to at least one entity such as the subject, a guardian of the subject, a physician, a medical organization, and a medical insurer. In other embodiments, it may be convenient to report results of monitoring, and/or efficacy of treatment and/or prophylactic methods to such entity.

In a specific embodiment of any of the above methods, the markers analyzed are REG3$\alpha$ and CRP.

In a specific embodiment of any of the above methods, expression levels of REG3$\alpha$ and CRP are detected using ELISA.

Therapeutic Methods of the Invention

In some aspects, provided herein are methods of treating endoscopically active gastrointestinal disease in a subject in need thereof.

In one aspect, provided herein is a method of treating endoscopically active gastrointestinal disease in a subject in need thereof, the method comprising:

selecting a subject having a REG3$\alpha$ or a combined REG3$\alpha$/CRP index score indicating the presence of endoscopically active gastrointestinal disease in the subject and administering to the selected subject a therapeutic agent under conditions effective to treat the endoscopically active gastrointestinal disease in the subject.

In some embodiments, selecting a subject having a REG3$\alpha$ or a combined REG3$\alpha$/CRP index score indicating the presence of endoscopically active gastrointestinal disease is determined by applying a diagnostic method described herein.

In some embodiments, the subject is treatment naïve for inflammatory bowel disease. In some embodiments of the above methods, the subject has undergone prior treatment with a therapeutic agent for inflammatory bowel disease. In some embodiments, the subject has undergone surgical resection as a treatment for inflammatory bowel disease.

Therapeutic agents suitable for use in the methods of the present disclosure include, but are not limited to, known IBD therapies including biologic agents, steroids, conventional drugs, nutritional supplements, and/or surgical procedures.

Biologic agents that may be used the methods of the present disclosure include, without anti-cytokine and chemokine antibodies such as anti-tumor necrosis factor alpha (TNF$\alpha$) antibodies. Examples of anti-TNF$\alpha$ antibodies include, but are not limited to, chimeric monoclonal antibodies such as Infliximab (REMICADE®) (Centocor, Inc.; Horsham, PA), which is a chimeric IgG1 anti-TNF$\alpha$ monoclonal antibody; humanized monoclonal antibodies such as CDP571 and the PEGylated CDP870; fully human monoclonal antibodies such as Adalimumab (HUMIRA®) (Abbott Laboratories; Abbott Park, IL); p75 fusion proteins such as Etanercept (ENBREL®) (Amgen; Thousand Oaks, CA, Wyeth Pharmaceuticals Inc.; Collegeville, PA); small molecules (e.g., MAP kinase inhibitors); and combinations thereof. See, Ghosh, Novartis Found Symp., 263:193-205 (2004), which is incorporated herein by reference in its entirety.

Other biologic agents include, e.g., anti-cell adhesion antibodies such as Natalizumab (TYSABRI®) (Elan Pharmaceuticals, Inc.; Dublin, Ireland, Biogen Idec; Cambridge, MA), which is a humanized monoclonal antibody against the cellular adhesion molecule α4-integrin, and MLN-02 (Millennium Pharmaceuticals; Cambridge, MA), which is a humanized IgG1 anti-α4β7-integrin monoclonal antibody; anti-T cell agents; anti-CD3 antibodies such as Visilizumab (NUVION®) (PDL BioPharma; Incline Village, NV), which is a humanized IgG2M3 anti-CD3 monoclonal antibody; anti-CD4 antibodies such as Priliximab (cM-T412) (Centocor, Inc.; Horsham, PA), which is a chimeric anti-CD4 monoclonal antibody; anti-IL-2 receptor alpha (CD25) antibodies such as Daclizumab (ZENAPAX®) BioPharma; incline Village, NV; Roche; Nutley, NJ), which is a humanized IgG1 anti-CD25 monoclonal antibody, and Basiliximab (SEVIULECT®) (Novartis; Basel, Switzerland), which is a chimeric IgG1 anti-CD25 monoclonal antibody; Vedolizurnab (ENTYVIO®) (Millennium Pharmaceuticals), which is a humanized antibody against integrin $\alpha_4\beta_7$; Ustekinumab (STELARA®) (Centocor), which is a humanized antibody against IL-12 and IL-23; and combinations thereof.

Non-limiting examples of conventional drugs include, aminosalicylates (e.g., mesalamines, mesalazine, sulfasalazine, and the like), corticosteroids (e.g., prednisone), thiopurines (e.g., azathioprine, 6-mercaptopurine, and the like), other immunomodulators (e.g., methotrexate, cyclosporine A and tacrolimus), free bases thereof, pharmaceutically acceptable salts thereof, derivatives thereof, analogs thereof, and combinations thereof.

Further therapeutic agents suitable for use in the methods of the present disclosure include targeted small molecule drugs such as anti-JAK kinase medications such as tofacitinib.

Additional therapeutic agents suitable for use in the methods of the present disclosure include those described in, e.g., Sands, Surg. Clin. North Am., 86:1045-1064 (2006); Danese et al., Mini Rev. Med. Chem., 6:771-784 (2006); Domenech, Digestion, 73 (Suppl. 1):67-76 (2006); Nakamura et al., World J. Gastroenterol., 12:4628-4635 (2006); and Gionchetti et al., World J. Gastroenterol., 12:3306-3313 (2006); each of which are incorporated herein by reference in their entirety for all purposes.

In some embodiments, the therapeutic agent is Adalimumab (HUMIRA®), Adalimumab-adbm (CYLTEZO®), Adalimumab-atto (AMJEVITA®), Certolizumab (CIMZIA®), Infliximab (REMICADE®), Infliximab-abda (RENFLEXIS®), Infliximab-dyyb (INFLECTRA®), Natalizumab (TYSABRI®), Ustekinumab (STELARA®), Vedolizumab (ENTYVIO®), upadacitinib, tofacitinib, Receptos, mesalamine, sulfasalazine, prednisone, azathioprine, mercaptopurine, and methotrexate, or any combination thereof.

In some embodiments of the above methods, the subject has an inflammatory bowel disease selected from the group consisting of Crohn's disease, colitis, ulcerative colitis, ileocolitis, ileitis, gastroduodenal Crohn's disease, jejunoileitis, and Crohn's colitis. In some embodiments, the subject has Crohn's disease. In some embodiments, the subject has ulcerative colitis.

In some embodiments, the therapeutic agent(s) is administered at a "therapeutically effective amount". A "therapeutically effective amount" refers to an amount effective, at dosages and for periods of time necessary, to achieve the desired therapeutic result. A therapeutically effective amount of the therapeutic agent(s) may vary according to factors such as the disease state, age, sex, and weight of the individual, and the ability of the therapeutic agent(s) to elicit a desired response in the individual. A therapeutically effective amount is also one in which any toxic or detrimental effects of the therapeutic agent(s) are outweighed by the therapeutically beneficial effects.

The therapeutic agent(s) may be administered to the subject via any suitable route of administration. The effective amount or dose of the therapeutic agent(s) administered should be sufficient to provide a therapeutic response in the subject over a reasonable time frame. For example, the dose of immunosuppressive drug should be sufficient to decrease symptoms of inflammatory bowel disease along with (i) decreasing the level of any of the biomarkers described herein as being associated with endoscopically active gastrointestinal disease and/or (ii) decreasing the index score value. The dose will be determined by the efficacy of the particular active agent and the condition of the subject (e.g., human), as well as the body weight of the subject (e.g., human) to be treated.

Dosage regimens may be adjusted to provide the optimum desired response (e.g., a therapeutic response). For example, a single bolus maybe administered, several divided doses maybe administered over time, or the dose maybe proportionally reduced or increased as indicated by the exigencies of the therapeutic situation. It may be advantageous to formulate parenteral compositions in dosage unit form for ease of administration and uniformity of dosage. Dosage unit form as used herein refers to physically discrete units suited as unitary dosages for the subjects (e.g., human) to be treated; each unit containing a predetermined quantity of the therapeutic agent(s) calculated to produce the desired therapeutic effect in association with the required pharmaceutical carrier. The specification for the dosage unit forms of the present disclosure are dictated by and directly dependent on (a) the unique characteristics of the therapeutic agent(s) and the particular therapeutic effect to be achieved, and (b) the limitations inherent in the art of compounding such an therapeutic agent(s) for the treatment of sensitivity in individuals.

In another aspect, provided herein is a method of determining effectiveness of a treatment for endoscopically active gastrointestinal disease in a subject, said method comprising:

detecting an expression level of REG3α or REG3α/CRP (i.e., REG3α and CRP) in a first biological sample from a subject before the subject is treated for endoscopically active gastrointestinal disease;

detecting an expression level of REG3α or REG3α/CRP in a second biological sample from the subject after the subject has received a treatment for the endoscopically active gastrointestinal disease; and comparing the expression level of REG3α or REG3α/CRP in the second biological sample to the expression level of REG3α or REG3α/CRP in the first biological sample to determine effectiveness of the treatment in the subject.

In some embodiments of the above method, the method further comprises: applying a statistical algorithm to the expression level of REG3α or REG3α/CRP in the first and second biological samples to produce an index score for endoscopically active gastrointestinal disease in the subject prior to said comparing. In some embodiments, the index score is a REG3α index score (i.e., generated based on REG3α level alone). In some embodiments, the index score is a combined REG3α/CRP index score (i.e., generated based on REG3α and CRP levels).

In further embodiments, the detecting step comprises determining the levels of one and more additional markers disclosed herein (e.g., ANG1, ANG2, CRP, SAA1, IL7, EMMPRIN, MMP1, MMP2, MMP3, MMP9, TGFA, CEACAM1, and/or VCAM1). In further embodiments, the method further comprises: applying a statistical algorithm to the expression level of REG3α or REG3α/CRP and one and more additional markers in the first and second biological samples to produce an integrated index score for endoscopically active gastrointestinal disease in the subject prior to the comparing step.

In some embodiments of the above methods, the expression level of REG3α or REG3α/CRP, optionally one and more additional markers, is compared by determining whether the index score for endoscopically active gastrointestinal disease in the first biological sample is different than the index score for endoscopically active gastrointestinal disease in the second biological sample.

In some embodiments, the method comprises determining the treatment is (1) effective when the index score for endoscopically active gastrointestinal disease in the first biological sample is higher than the index score for endoscopically active gastrointestinal disease in the second biological sample; and (2) not effective when the index score for endoscopically active gastrointestinal disease in the first biological sample is lower than or equal to the index score for endoscopically active gastrointestinal disease in the second biological sample. If determined not effective, the treatment may be adjusted or changed.

In some embodiments of the above methods, the subject has an inflammatory bowel disease selected from the group consisting of Crohn's disease, colitis, ulcerative colitis, ileocolitis, ileitis, gastroduodenal Crohn's disease, jejunoileitis, and Crohn's colitis. In some embodiments, the subject has Crohn's disease. In some embodiments, the subject has ulcerative colitis.

In some embodiments of the above methods, the treatment involves administering a therapeutic agent selected from the biologic agents, steroids, conventional drugs, nutritional supplements, and/or surgical procedures described above.

In some embodiments, the methods of the present disclosure can also be used for selecting a suitable therapeutic agent for the treatment of the endoscopically active gastrointestinal disease such as a particular biologic agent and/or conventional drug described herein.

In some embodiments, the treatment involves administering a therapeutic agent selected from the group consisting of Adalimumab (HUMIRA®), Adalimumab-adbm (CYLTEZO®), Adalimumab-atto (AMJEVITA®), Certolizumab (CIMZIA®), Infliximab (REMICADE®), Infliximab-abda (RENFLEXIS®), Infliximab-dyyb (INFLECTRA®), Natalizumab (TYSABRI®), Ustekinumab (STELARA®), Vedolizumab (ENTYVIO®), upadacitinib, tofacitinib, Receptos, mesalamine, sulfasalazine, prednisone, azathioprine, mercaptopurine, and methotrexate.

A subject can also be monitored at periodic time intervals to assess the effectiveness of a certain therapeutic regimen once diagnostic and/or prognostic information has been obtained from the subject's sample. For example, the level of the markers (e.g., REG3α) may change based on the therapeutic effect of a treatment such as a biologic agent. In some embodiments, the patient can be monitored to assess response and understand the effects of certain treatments in an individualized approach. Additionally, patients may not respond to a treatment, but the markers may change, suggesting that these patients belong to a special population (not responsive) that can be identified by their marker levels. These patients can be discontinued on their current therapy and alternative treatments can be prescribed.

A subject can also be monitored at periodic time intervals to assess the levels of various markers. The marker levels at various time points, as well as the rate of change of the marker levels over time may be informative. In certain instances, the rate of increase of a marker(s) in an individual over a certain threshold amount indicates the individual has a higher risk of developing complications or risk of undergoing surgery. Information obtained from serial testing in the form of a marker velocity (i.e., the change in marker level over a time period) can be associated with the severity of the disease, the risk of complications of disease, and the risk of undergoing surgical treatment.

In some embodiments of the above methods, the biological sample is whole blood, plasma, serum, urine, saliva, sputum, bronchial lavage fluid, tears, or stool. In some embodiments, the biological sample is a biofluid sample (e.g., whole blood, plasma, serum, saliva, or urine). In some embodiments, the biological sample is serum.

In various embodiments of the above methods, the subject is a mammalian subject. In some embodiments, the subject is a human.

Kits of the Invention

The present disclosure also provides kits useful in the practice of the methods described herein. In some embodiments, these kits comprise detection reagents that specifically bind the biomarkers described herein, such as for example and not limitation, REG3α and optionally CRP. The kits typically include a probe that comprises an antibody or nucleic acid sequence that specifically binds to polypeptides or polynucleotides described herein, such as for example and not limitation, REG3α and optionally CRP, as well as genes encoding these biomarkers, and a label for detecting the presence of the probe. The kits may include several antibodies specific for, or polynucleotide sequences encoding, the polypeptides described herein. The kits may further comprise control probes for detection of a control nucleic acid or a control protein in order to provide a control level of the nucleic acid or protein, and/or other standards or controls. The probe is optionally detectably labeled.

The kit may contain in separate containers a nucleic acid or antibody (either already bound to a solid matrix or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions for carrying out the assay may also be included in the kit. The assay may, for example and not limitation, be in the form of a Northern hybridization, sandwich ELISA or protein antibody array.

Reagents for detecting biomarkers described herein can be immobilized on a solid matrix such as a porous strip to form at least one biomarker detection site. The measurement or detection region of the porous strip may include a plurality of sites containing an antibody or nucleic acid. A test strip may also contain sites for negative and/or positive controls. Alternatively, control sites can be located on a separate strip from the test strip. Optionally, the different detection sites may contain different amounts of immobilized antibodies or nucleic acids, e.g., a higher amount in the first detection site and lesser amounts in subsequent sites.

Upon the addition of test sample, the number of sites displaying a detectable signal provides a quantitative indication of the amount of biomarker present in the sample. The detection sites may be configured in any suitably detectable shape and are typically in the shape of a bar or dot spanning the width of a test strip.

Alternatively, the kit contains a nucleic acid substrate array comprising one or more nucleic acid sequences. The nucleic acids on the array specifically identify one or more nucleic acid sequences adapted to bind a nucleic acid sequence encoding a biomarker described herein. The substrate array can be on, e.g., a solid substrate or "chip". Alternatively, the substrate array can be a solution array.

A kit of the invention can also provide reagents for primer extension and amplification reactions. For example, in some embodiments, the kit may further include one or more of the following components: a reverse transcriptase enzyme, a DNA polymerase enzyme (such as, e.g., a thermostable DNA polymerase), a polymerase chain reaction buffer, a reverse transcription buffer, and deoxynucleoside triphosphates (dNTPs).

Alternatively (or in addition), a kit can include reagents for performing a hybridization assay for nucleic acid(s) and/or proteins. The detecting agents can include nucleotide analogs and/or a labeling moiety, e.g., directly detectable moiety such as a fluorophore (fluorochrome) or a radioactive isotope, or indirectly detectable moiety, such as a member of a binding pair, such as biotin, or an enzyme capable of catalyzing a non-soluble colorimetric or luminometric reaction. In addition, the kit may further include at least one container containing reagents for detection of electrophoresed nucleic acids. Such reagents include those which directly detect nucleic acids, such as fluorescent intercalating agent or silver staining reagents, or those reagents directed at detecting labeled nucleic acids, such as, but not limited to, ECL reagents. A kit can further include DNA or RNA isolation or purification means as well as positive and negative controls. Alternatively, the kit may include at least one container containing reagents for detection of electrophoresed proteins. Such reagents include those which directly detect proteins, such as Coomassie blue or other staining reagents including fluorescent staining agents, or those reagents directed at detecting labeled proteins. A kit can further include protein isolation or purification means as well as positive and negative controls. A kit can also include a notice associated therewith in a form prescribed by a governmental agency regulating the manufacture, use or sale of diagnostic kits. Detailed instructions for use, storage and trouble-shooting may also be provided with the kit. A kit can also be optionally provided in a suitable housing that is preferably useful for robotic handling in a high throughput setting.

The components of the kit may be provided as dried powder(s). When reagents and/or components are provided as a dry powder, the powder can be reconstituted by the addition of a suitable solvent. It is envisioned that the solvent may also be provided in another container. The container will generally include at least one vial, test tube, flask, bottle, syringe, and/or other container means, into which the solvent is placed, optionally aliquoted. The kits may also comprise a second container means for containing a sterile, pharmaceutically acceptable buffer and/or other solvent.

Where there is more than one component in the kit, the kit also will generally contain a second, third, or other additional container into which the additional components may be separately placed. However, various combinations of components may be comprised in a container.

Such kits may also include components that preserve or maintain DNA or RNA, such as reagents that protect against nucleic acid degradation. Such components may be nuclease or RNase-free or protect against RNases, for example. Such kits may also include components that preserve or maintain proteins, such as reagents that protect against protein degradation. Any of the compositions or reagents described herein may be components in a kit.

In some embodiments, the kit further comprises an apparatus for collecting a blood sample from a subject. In other embodiments, the kit further comprises instructions for using the collection apparatus and/or the reagents comprising the kit.

Computer-Implemented Aspects

As understood by those of ordinary skill in the art, the methods and information described herein may be implemented, in all or in part, as computer executable instructions on known computer readable media. For example, the methods described herein may be implemented in hardware. Alternatively, the methods may be implemented in software stored in, for example, one or more memories or other computer readable medium and implemented on one or more processors. As is known, the processors may be associated with one or more Controllers, calculation units and/or other units of a computer system, or implanted in firmware as desired. If implemented in software, the routines may be stored in any computer readable memory such as in RAM, ROM, flash memory, a magnetic disk, a laser disk, or other storage medium, as is also known. Likewise, this software may be delivered to a computing device via any known delivery method including, for example, over a communication channel such as a telephone line, the Internet, a wireless connection, etc., or via a transportable medium, such as a computer readable disk, flash drive, and the like.

More generally, and as understood by those of ordinary skill in the art, the various steps described above may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any known computer readable medium such as on a magnetic disk, an optical disk, or other storage medium, in a RAM or ROM or flash memory of a computer, processor, hard disk drive, optical disk drive, tape drive, etc. Likewise, the software may be delivered to a user or a computing system via any known delivery method including, for example, on a computer readable disk or other transportable computer storage mechanism.

Thus, another aspect of the disclosure is a system that is capable of carrying out a part or all of a method of the disclosure, or carrying out a variation of a method of the disclosure as described herein in greater detail. Exemplary systems include, as one or more components, computing systems, environments, and/or configurations that may be suitable for use with the methods and include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like. In some variations, a system of the disclosure includes one or more machines used for analysis of biological material (e.g., genetic material), as described herein. In some variations, this analysis of the biological material involves a chemical analysis and/or a nucleic acid amplification.

The computer may operate in a networked environment using logical connections to one or more remote computers, such as a remote computer via a network interface controller (NIC). The remote computer may be a personal computer, a server, a router, a network PC, a peer device or other common network node, and typically includes many or all of the elements described above relative to the computer. The logical connection between the NIC and the remote computer may include a local area network (LAN), a wide area network (WAN), or both, but may also include other networks. Such networking environments are commonplace in offices, enterprise-wide computer networks, intranets, and the Internet. The remote computer may also represent a web server supporting interactive sessions with the computer; or in the specific case of location-based applications may be a location server or an application server.

In some embodiments, the network interface may use a modem when a broadband connection is not available or is not used. It will be appreciated that the network connection shown is exemplary and other means of establishing a communications link between the computers may be used.

In some embodiments, the disclosed methods involve the use of a statistical algorithm or process to classify the subject as having endoscopically active gastrointestinal disease or being in endoscopic remission. The statistical algorithm or process may comprise one or more learning statistical classifier systems. As used herein, the term "learning statistical classifier system" includes a machine learning algorithmic technique capable of adapting to complex data sets (e.g., panel of markers of interest and/or presence of IBD-related symptoms) and making decisions based upon such data sets. In some embodiments, a single learning statistical classifier system is used. In other embodiments, a combination of 2, 3, 4, 5, 6, 7, 8, 9, 10, or more learning statistical classifier systems are used, e.g., in tandem. Examples of learning statistical classifier systems include, but are not limited to, those using inductive learning (e.g., decision/classification trees such as random forests, classification and regression trees (CART), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naïve learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems including support vector machines (e.g., Kernel methods), multivariate adaptive regression splines (MARS), Levenberg-Marquardt algorithms, Gauss-Newton algorithms, mixtures of *Gaussians*, gradient descent algorithms, and learning vector quantization (LVQ) may also be utilized.

In some instances, the data obtained from using the learning statistical classifier system or systems can be pro-cessed using a processing algorithm. Various processing algorithm can be selected, such as a multiplayer perceptron, backpropagation network, and Levenberg-Marquardt algorithm. In other instances, a combination of such processing algorithms can be used, such as in a parallel or serial fashion.

The term "statistical algorithm" or "statistical process" includes any of a variety of statistical analyses used to determine relationships between variables. In the present invention, the variables are the level of at least one marker of interest and/or the presence of endoscopically active gastrointestinal disease. The number of markers analyzed using a statistical algorithm described herein may be 1, 2, 3, 4, 5, 6, 7, 8, 9, 10 or more. In one embodiment, logistic regression is used. In another embodiment, linear regression is used. In some embodiments, the statistical algorithms of the present disclosure can use a quantile measurement of a particular marker within a given population as a variable. Quantiles are a set of "cut points" that divide a sample of data into groups containing (as far as possible) equal numbers of observations. For example, quartiles are values that divide a sample of data into four groups containing (as far as possible) equal numbers of observations. The lower quartile is the data value a quarter way up through the ordered data set; the upper quartile is the data value a quarter way down through the ordered data set. Quintiles are values that divide a sample of data into Live groups containing (as far as possible) equal numbers of observations. The present invention can also include the use of percentile ranges of marker levels (e.g., tertiles, quartile, quintiles, etc.), or their cumulative indices (e.g., quartile sums of marker levels, etc.) as variables in the algorithms (just as with continuous variables).

The learning statistical classifier systems described herein can be trained and tested using a cohort of samples (e.g., serum samples) from TBD subjects having endoscopically active gastrointestinal disease (e.g., SES-CD>3) and IBD subjects being in remission (e.g., SES-CD≤3). For example, samples from patients diagnosed by a physician, and preferably by a gastroenterologist as having endoscopically active gastrointestinal disease using a biopsy, colonoscopy, or an immunoassay as described in, e.g., U.S. Pat. No. 6,218,129, are suitable for use in training and testing the learning statistical classifier systems of the present invention. Samples from patients diagnosed with IBD can also be stratified into Crohn's disease or ulcerative colitis using an immunoassay as described in, e.g., U.S. Pat. Nos. 5,750,355 and 5,830,675. One skilled in the art will know of additional techniques and diagnostic criteria for obtaining a cohort of patient samples that can be used in training and testing the learning statistical classifier systems of the present disclosure.

The use of learning statistical classifier systems may provide improved sensitivity, specificity, negative predictive value, positive predictive value, and/or overall accuracy for classifying whether a subject is having endoscopically active gastrointestinal disease or in endoscopic remission.

As used herein, the term "sensitivity" refers to the probability that a diagnostic method of the present disclosure gives a positive result when the sample is positive, e.g., having endoscopically active gastrointestinal disease. Sensitivity is calculated as the number of true positive results divided by the sum of the true positives and false negatives. Sensitivity essentially is a measure of how well a method of the present disclosure correctly identifies those with endoscopically active gastrointestinal disease from those being in endoscopic remission. In some embodiments, the statistical algorithms can be selected such that the sensitivity of classifying endoscopically active gastrointestinal disease is at least about 60%, and can be, for example, at least about 65%, 70%, 75%, 76%, 77%, 78%, 79%, 80%, 81%, 82%, 83%, 84%, 85%, 86%, 87%, 88%. 89%, 90%, 91%, 92%, 93%, 94%, 95%, 96%, 97%. 98%, or 99%.

The term "specificity" refers to the probability that a diagnostic method of the present disclosure gives a negative result when the sample is not positive, e.g., being in endoscopic remission. Specificity is calculated as the number of true negative results divided by the sum of the true negatives and false positives. Specificity essentially is a measure of how well a method of the present disclosure excludes those who are in endoscopic remission from those who have endoscopically active gastrointestinal disease. In some embodiments, the statistical algorithms can be selected such that the specificity of classifying endoscopically active gastrointestinal disease is at least about 40%, for example, at least about 45%, 50%, 55%, 60%, 65%, 70%, 75%, 80%, 85%, 86%, 87%. 88%, 89%. 90%, 91%, 92%, 93%, 94%. 95%, 96%, 97%, 98%, or 99%.

As used herein, the term "negative predictive value" or "NPV" refers to the probability that an individual identified as not having endoscopically active gastrointestinal disease actually does not have the disease. Negative predictive value can be calculated as the number of true negatives divided by the sum of the true negatives and false negatives. Negative predictive value is determined by the characteristics of the diagnostic method as well as the percentage of the disease in the population analyzed. In some embodiments, the statistical algorithms can be selected such that the negative predictive value in a population having a disease percentage is in the range of about 60% to about 99% and can be, for example, at least about 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "positive predictive value" or "PPV" refers to the probability that an individual identified as having endoscopically active gastrointestinal disease actually has the disease. Positive predictive value can be calculated as the number of true positives divided by the sum of the true positives and fake positives. Positive predictive value is determined by the characteristics of the diagnostic method as well as the percentage of the disease in the population analyzed. In some embodiments, the statistical algorithms can be selected such that the positive predictive value in a population having a disease percentage is in the range of about 50% to about 99% and can be, for example, at least about 50%, 55%, 60%, 65%, 70%, 75%, 80%, 85%, 86%, 87%, 88%, 89%, 90%, 91%, 92%, 93%, 94%, 95%, 96%, 97%, 98%, or 99%.

Predictive values, including negative and positive predictive values, are influenced by the percentage of the disease in the population analyzed. In the methods of the present disclosure, the statistical algorithms can be selected to produce a desired clinical parameter for a clinical population with a particular IBD percentage. For example, learning statistical classifier systems can be selected for an IBD percentage of up to about 1%, 7%, 3%, 4%, 5%, 6%, 7%, 8%, 9%, 10%, 15%, 20%, 25%, 30%. 35%, 40%. 45%, 50%, 55%, 60%, 65%, or 70%, which can be seen, e.g., in a clinician's office such as a gastroenterologist's office or a general practitioner's office.

As used herein, the term "overall agreement" or "overall accuracy" refers to the accuracy with which a method of the present disclosure classifies a disease state. Overall accuracy is calculated as the sum of the true positives and true negatives divided by the total number of sample results and is affected by the percentage of the disease in the population analyzed. The "overall agreement" or "overall accuracy" may be indicated by the Area Under the Curve (AUC) in a ROC curve. For example, the statistical algorithms can be selected such that the overall accuracy in a patient population having a disease percentage is at least about 60%, and can be, for example, at least about 65%, 70%, 75%, 76%, 77%, 78%, 79%, 80%, 81%, 82%, 83%, 84%, 85%, 86%, 87%, 88%, 89%, 90%, 91%, 97%, 93%, 94%. 95%. 96%, 97%, 98%, or 99%.

EXAMPLES

The examples below are intended to exemplify the practice of embodiments of the disclosure but are by no means intended to limit the scope thereof.

Materials and Methods

Serum samples. The Mount Sinai Crohn's and Colitis Registry (MSCCR) was utilized. All patients with Crohn's disease (CD) who had a blood sample at the time of a colonoscopy at which an SES-CD score was performed were included. Serum samples were collected prospectively under protocols approved by the Icahn School of Medicine at Mount Sinai Institutional Review Board and stored at −80° C.

Biomarkers. A set of graft-versus-host-disease (GVHD) biomarkers (REG3α, TNF, CRP, and ST2) were assayed to determine their performance at diagnosing active versus inactive CD using SES-CD scores as the gold standard. Endoscopic remission was defined as an SES-CD score ≤3.

REG3α detection. REG3α ELISA kits were purchased from MBL International (Ab-Match Assembly Human PAP1 (REG3α) kit and Ab-Match Universal kit), and measurements were performed according to the manufacturer's protocol. Samples (diluted 1:10) and standards were run in duplicate, absorbance was measured with a SpectraMax® M2 (Molecular Devices), and results were calculated with SoftMax® Pro Version 5.4 (Molecular Devices).

Modeling. Logistic regression was used to model SES-CD categories (SES-CD>3 versus ≤3) and biomarkers. After the univariate analyses and the correlation analyses (Table 1), log REG3α and log CRP were kept in the model to predict the SES-CD categories.

TABLE 1

| Correlation Analyses in Patients with Remission. | | | | |
|---|---|---|---|---|
| | Total SES-CD | CRP | ST2 | TNF |
| CRP | 0.30* (p < 0.001) | | | |
| ST2 | 0.03 | −0.007 | | |
| TNF | 0.07 | 0.009 | 0.68* (p < 0.001) | |
| REG3α | 0.16* (p = 0.01) | −0.02 | 0.07 | 0.08 |

Figure 2:
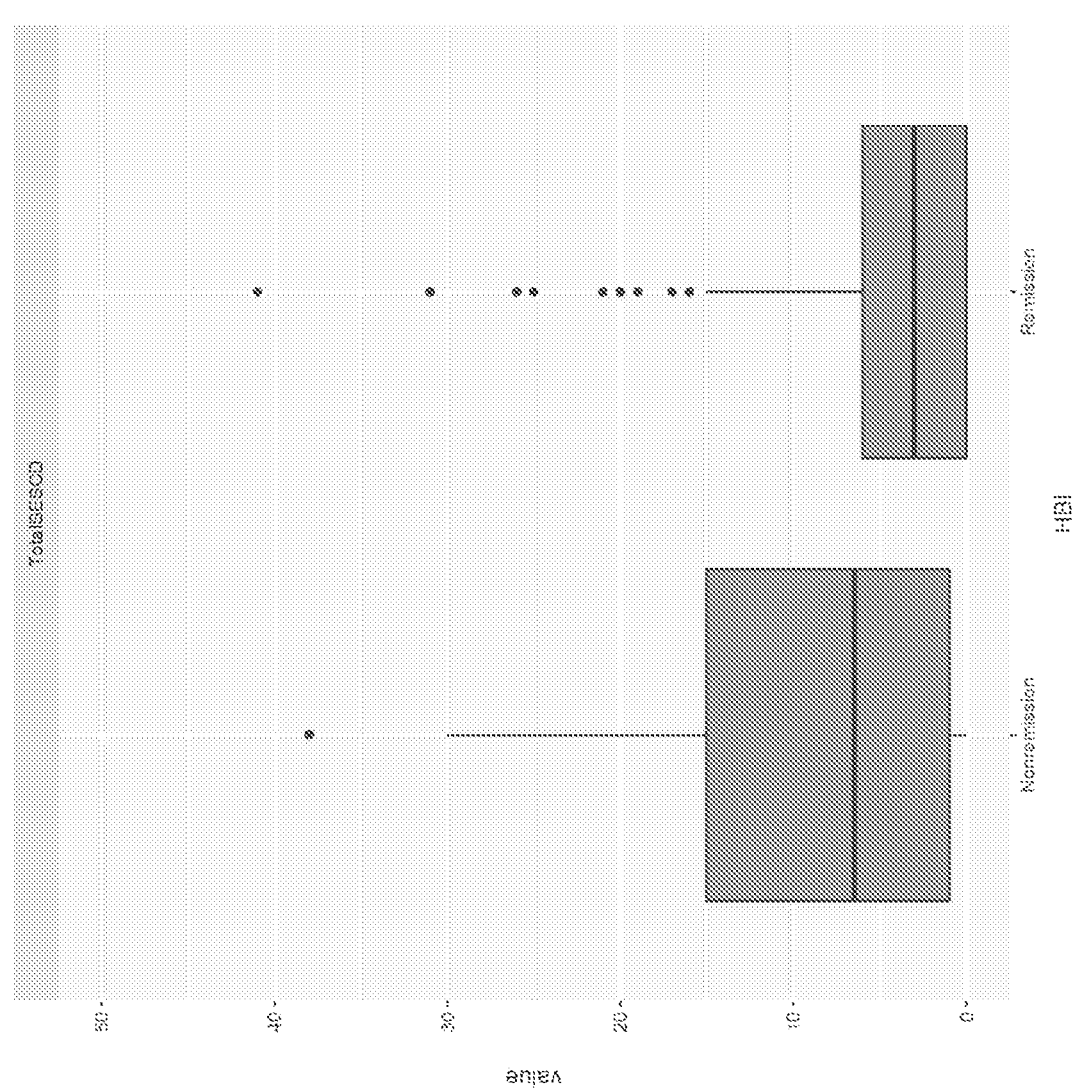
FIG. 2 is a graph showing boxplots of total Simple Endoscopic Score for Crohn's Disease (SES-CD) scores of patients under HBI non-remission or HBI remission. P-value between the HBI groups: 0.0001.
Figure 3:
FIG. 3 is a bar graph showing the percentage of patients having total SES-CD>3 under HBI non-remission or HBI remission. This highlights the discrepancy between clinical (symptom based) remission and objective (endoscopic) remission. P-value (SES-CD groups versus HBI groups)= 0.005.

Example 1—REG3α, TNF, CRP, and ST2 Serum Expression Levels in CD Patients in HBI Remission or HBI Non-Remission Serum expression levels of GVHD biomarkers (REG3α, TNF, CRP, and ST2) were first assayed in a total of 351 CD patients in HBI remission or HBI non-remission (defined as a Harvey Bradshaw Index, HBI, score <5) (FIG. 1). REG3α, TNF, and CRP were observed to be significantly associated with endoscopic activity. As shown in FIG. 2, there are a wide range of SES-CD scores in patients with (HBI non-remission) and without (HBI remission) symptoms. FIG. 3 shows that a significant percentage (>40%) of CD patients without symptoms (HBI remission) actually have active disease (SES-CD score >3) on colonoscopy in this cohort. These results are consistent with prior data demonstrating that clinical symptoms frequently do not correlate well with objective metrics of inflammation, in particular endoscopically active disease (Peyrin-Biroulet et al., "Clinical Disease Activity, C-Reactive Protein Normalisation and Mucosal Healing in Crohn's Disease in the SONIC Trial," *Gut.* 63(1):88-95 (2014), which is hereby incorporated by reference in its entirety).

Figure 4:
FIG. 4 is a graph showing boxplots of log-transformed serum biomarker concentrations (TNF, ST2, REG3α, and CRP) in patients under non-remission by SES-CD scores. P-values between the SES-CD groups: p-value (log TNF) =0.097, p-value (log ST2)=0.052, p-value (log REG3α) =0.004, and p-value (log CRP)=0.0002.
Figure 5:
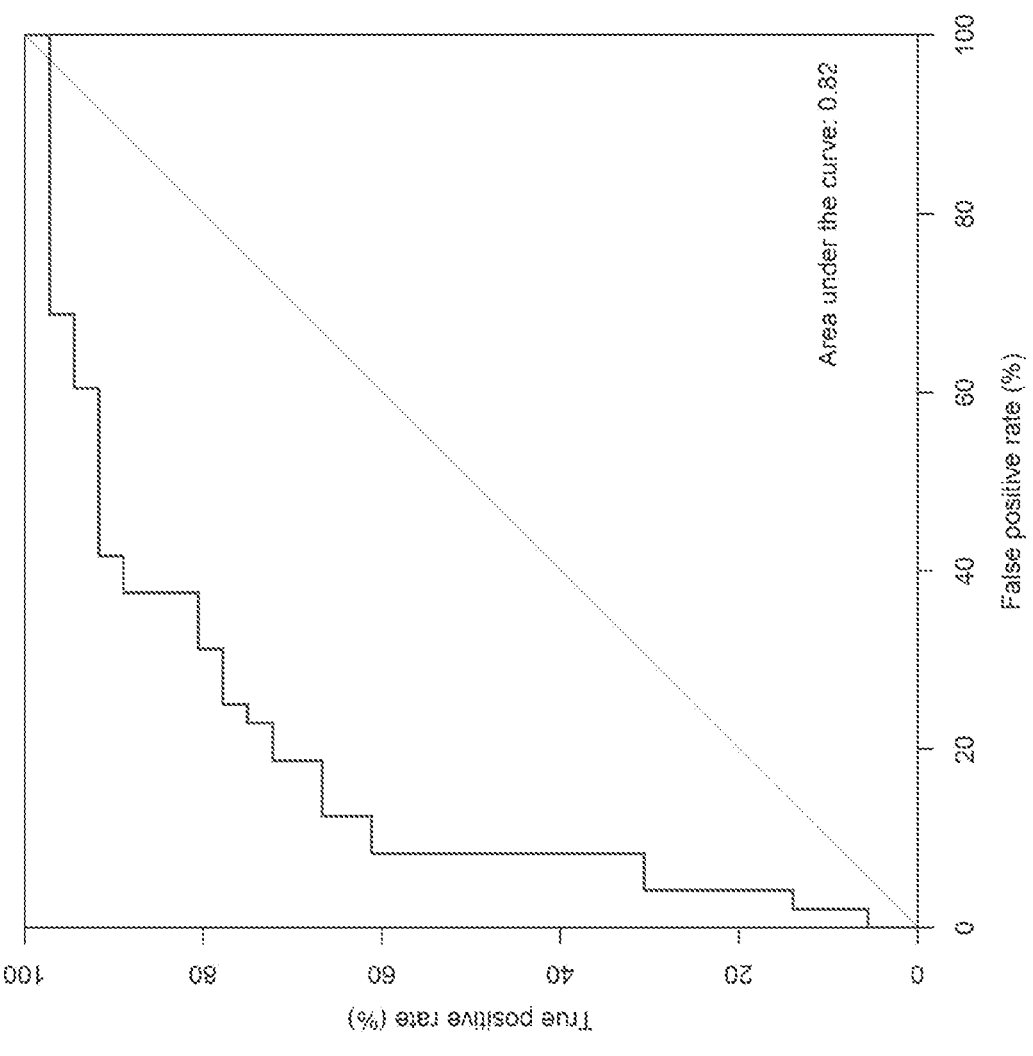
FIG. 5 is a plot of true positive rate (sensitivity) versus the false positive rate (1−specificity) with a Receiver Operating Characteristic Curve (ROC curve) using the test dataset. The model is SES-CD~1.045*log$_{10}$ REG3α+0.667*log$_{10}$ CRP. Both REG3α and CRP are significant in the model with p-values equal to 0.038 and 0.011, respectively.
Figure 6:
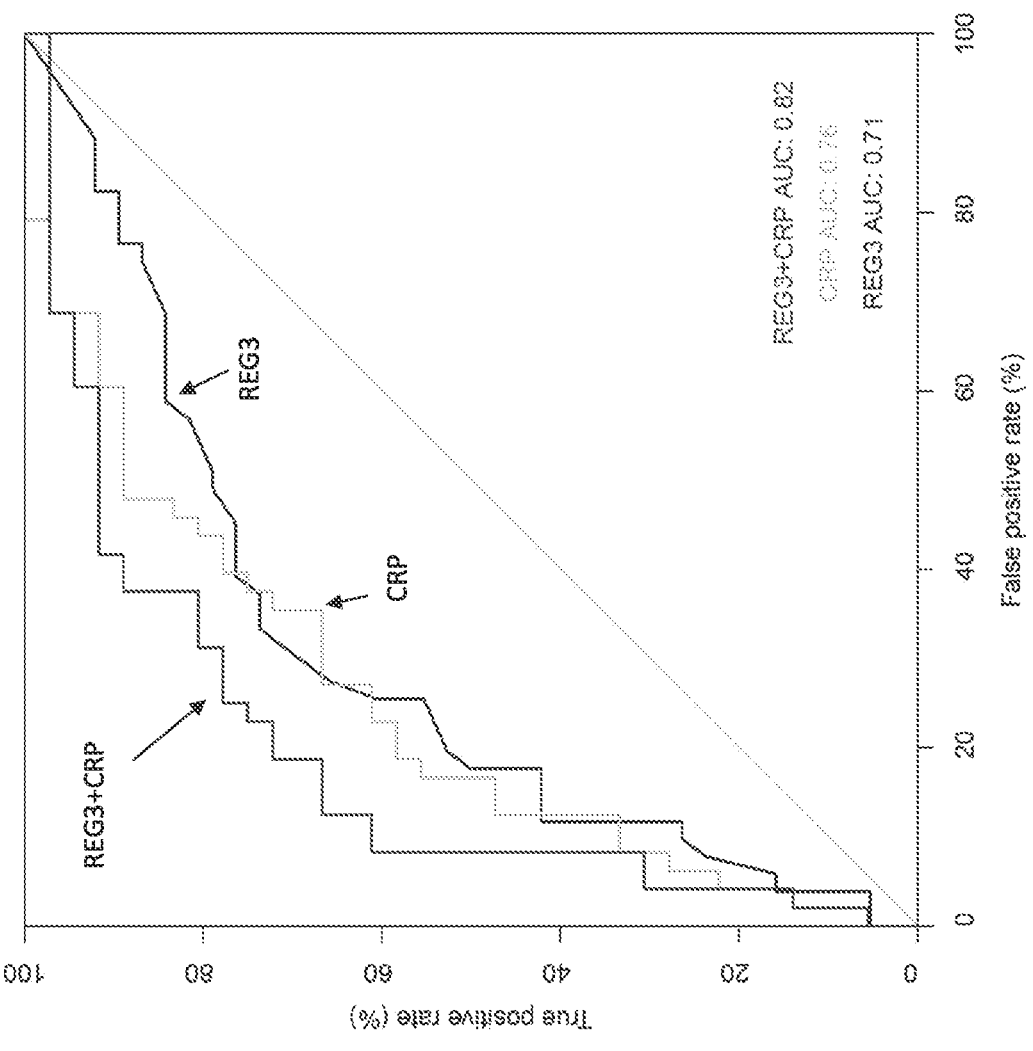
FIG. 6 is a plot of true positive rate versus the false positive rate showing individual ROC curves and Area Under the Curve (AUC) values of REG3α and CRP individually compared to a composite AUC of REG3α and CRP.

Example 2—Development and Evaluation of a Statistical Algorithm Relating REG3α and CRP Serum Levels to Endoscopically Active Disease Given that patients with symptoms (HBI≥5) often undergo colonoscopy or have treatment changes regardless Patients were randomly divided into two groups, with ⅔ used in a training set and ⅓ used as a testing set. Next, serum levels of REG3α, TNF, CRP, and ST2 were evaluated in the training set and the results were stratified by endoscopic remission (SES-CD≤3 versus SES-CD>3). Higher concentrations of REG3α and CRP was observed in non-remission CD patients (FIG. 4). Next, the ability of the combination of REG3α and CRP to predict endoscopic remission was evaluated and found to have good performance, with an AUC of 0.82 (FIG. 5). The model shown in FIG. 5 is SES-CD~1.045*$\log_{10}$ REG3α+0.667*$\log_{10}$ CRP. The CRP value used in the model is in mg/L. When looking at REG3α and CRP alone, REG3α was observed to have good discriminate capacity by itself (AUC=0.71), but the combination of REG3α and CRP provided greater accuracy (AUC=0.82) (FIG. 6). Table 3 provides performance characteristics at different cut-offs.

TABLE 3

Sensitivity (True Positive Fraction), Specificity (True Negative Fraction), Positive Predicted Values (PPV), and Negative Predicted Value (NPV) based on Different Thresholds Applied to the Predicted Probabilities[1].

| | Training Set | | | | | Test Set | | | | |
|---|---|---|---|---|---|---|---|---|---|---|
| Threshold | % of patients estimated to have SES-CD > 3 | Sensitivity | Specificity | PPV | NPV | % of patients estimated to have SES-CD > 3 | Sensitivity | Specificity | PPV | NPV |
| 0.35 | 0.72 | 0.80 | 0.34 | 0.47 | 0.69 | 0.70 | 0.92 | 0.46 | 0.56 | 0.88 |
| 0.36 | 0.72 | 0.80 | 0.35 | 0.47 | 0.70 | 0.68 | 0.92 | 0.50 | 0.58 | 0.89 |
| 0.37 | 0.69 | 0.80 | 0.39 | 0.49 | 0.72 | 0.65 | 0.92 | 0.54 | 0.60 | 0.90 |
| 0.38 | 0.66 | 0.74 | 0.41 | 0.48 | 0.69 | 0.62 | 0.89 | 0.58 | 0.61 | 0.88 |
| 0.39 | 0.62 | 0.74 | 0.47 | 0.51 | 0.71 | 0.60 | 0.89 | 0.63 | 0.64 | 0.88 |
| 0.40 | 0.57 | 0.68 | 0.51 | 0.50 | 0.68 | 0.56 | 0.81 | 0.63 | 0.62 | 0.81 |
| 0.41 | 0.54 | 0.65 | 0.54 | 0.51 | 0.68 | 0.55 | 0.81 | 0.65 | 0.63 | 0.82 |
| 0.42 | 0.52 | 0.62 | 0.56 | 0.51 | 0.67 | 0.55 | 0.81 | 0.65 | 0.63 | 0.82 |
| 0.43 | 0.49 | 0.61 | 0.59 | 0.52 | 0.67 | 0.54 | 0.81 | 0.67 | 0.64 | 0.82 |
| 0.44 | 0.47 | 0.58 | 0.61 | 0.52 | 0.67 | 0.51 | 0.78 | 0.69 | 0.65 | 0.81 |

[1]Predicted probability is the probability of a patient having the outcome (SES-CD score > 3). This is estimated based on the model developed using the training set.

of non-invasive findings, analyses were next limited to 269 patients who had no symptoms (HBI<5) at the time of colonoscopy. Table 2 describes the baseline characteristics of the patients with HBI<5 at the time of colonoscopy (as well as the excluded patients who had symptoms). The values presented in Table 2 that are less 1 are observed percentages in indicated patient groups.

TABLE 2

Characteristics of Cohorts

| Variable | All HBI ≥ 5 | All HBI < 5 | Training Remission | Test Remission |
|---|---|---|---|---|
| Size | 82 | 269 | 180 | 89 |
| Inflammatory behavior | 0.77 | 0.73 | 0.71 | 0.76 |
| Stricturing behavior | 0.16 | 0.22 | 0.24 | 0.16 |
| Fistulizing behavior | 0.07 | 0.06 | 0.04 | 0.08 |
| Ileal location | 0.23 | 0.26 | 0.26 | 0.28 |
| Colonic location | 0.38 | 0.3 | 0.32 | 0.27 |
| Ileocolonic location | 0.39 | 0.43 | 0.43 | 0.45 |
| SESCD > 3 | 0.61 | 0.42 | 0.42 | 0.43 |

Discussion of Examples 1-2

The test described above has a similar AUC as compared to the blood test described in D'Haens G et al[1], but with fewer markers. This test is potentially more streamlined (1 or 2 markers as opposed to 11 markers) and can serve as a cheaper alternative to presently available tests.

Further, FIGS. 5 and 6 show the diagnostic accuracy of CRP+Reg3 combined (FIG. 5) and demonstrate that individually the markers perform well but there is synergistic effect when combining the markers (FIG. 6).

REFERENCES

1. D'Haens G et al. Gastroenterology 2020; 158:515-526
2. Tsuchida et al., Biochemistry and Biophysics Reports 2017; 12(C):198-205
3. Van Beelen Granlund et al., Cell Tissue Res. 2013; 352(3):639-46
4. Bajic et al., J Crohns Colitis. 2020; 14(10):1462-1472.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. A method for detecting Crohn's disease in a human subject, said method comprising:

(a) detecting, in a biological sample from the human subject, an expression level of regenerating islet-derived protein 3 alpha (REG3α) and an expression level of C-reactive protein (CRP), the biological sample comprising at least one of a serum sample or a whole blood sample;

(b) applying a statistical algorithm to said expression levels of REGα and CRP to generate a combined REG3α/CRP index score;

(c) determining that the human subject has or is likely to have Crohn's disease based on the combined REG3α/CRP index score being higher than an optimal classification threshold detecting the Crohn's disease in the subject; and (d) administering to the human subject a therapeutic agent under conditions effective to treat Crohn's disease in the human subject.

2. The method according to claim 1, wherein the statistical algorithm is $\log[p/(1-p)]=-2.140+1.045$ $(\log_{10}REG3\alpha)+0.667$ $(\log_{10}CRP)$ and the combined REG3α/CRP index score is the probability (p) obtained from said statistical algorithm.

3. The method according to claim 2, wherein the optimal classification threshold is selected from 0.35, 0.36, 0.37, 0.38, 0.39, 0.40, 0.41, 0.42, 0.43 and 0.44.

4. The method according to claim 2, wherein the optimal classification threshold is about 0.39.

5. The method according to claim 1, wherein the subject is treatment naïve for the Crohn's disease.

6. The method according to claim 1, wherein the subject of has undergone treatment for Crohn's disease.

7. The method according to claim 6, wherein the subject has undergone treatment with a therapeutic agent selected from the group consisting of Adalimumab, Adalimumab-adbm, Adalimumab-atto, Certolizumab, Infliximab, Infliximab-abda, Infliximab-dyyb, Ustekinumab, Vedolizumab, upadacitinib, tofacitinib, Receptos, mesalamine, sulfasalazine, prednisone, azathioprine, mercaptopurine, methotrexate, or a surgical resection.

8. The method of claim 1, wherein the biological sample is a plasma, urine, saliva, sputum, bronchial lavage fluid, tears, or stool sample.

9. The method according to claim 1, wherein said detecting is carried out using an enzyme-linked immunosorbent assay (ELISA), a collaborative enzyme enhanced reactive immunoassay (CEER), a homogenous mobility shift assay (HMSA), an immunohistochemical assay, fluorescence activated cell sorting (FACS), or a Western blot.

10. The method according to claim 1, wherein the therapeutic agent is selected from the group consisting of Adalimumab, Adalimumab-adbm, Adalimumab-atto, Certolizumab, Infliximab, Infliximab-abda, Infliximab-dyyb, Ustekinumab, Vedolizumab, upadacitinib, tofacitinib, Receptos, mesalamine, sulfasalazine, prednisone, azathioprine, mercaptopurine, and methotrexate.

11. A method of determining effectiveness of a treatment of Crohn's disease in a human subject, said method comprising:

detecting expression levels of regenerating islet-derived protein 3 alpha or (REG3α) and C-reactive protein (CRP) in a first biological sample from the human subject before the human subject receives the treatment for the Crohn's disease;

applying a statistical algorithm to said expression levels of REGα and CRP in the first biological sample to generate a first combined REG3α/CRP index score;

detecting expression levels of REG3α and CRP in a second biological sample from the human subject after the subject has received the treatment for the Crohn's disease;

applying a statistical algorithm to said expression levels of REGα and CRP in the second biological sample to generate a second combined REG3α/CRP index score; and comparing the second combined REG3α/CRP index score to the first combined REG3α/CRP index score to determine effectiveness of the treatment in the human subject.

12. The method according to claim 11, further comprising:

determining the treatment is effective based on the first combined REG3α/CRP index score being higher than the second combined REG3α/CRP index score.

13. The method according to claim 11, further comprising:

determining that the treatment is not effective based on the first combined REG3α/CRP index score being lower than or equal to the second combined REG3α/CRP index score; and at least one of adjusting or changing the treatment.

14. The method according to claim 11, wherein the therapeutic agent is selected from the group consisting of Adalimumab, Adalimumab-adbm, Adalimumab-atto, Certolizumab, Infliximab, Infliximab-abda, Infliximab-dyyb, Ustekinumab, Vedolizumab, upadacitinib, tofacitinib, Receptos, mesalamine, sulfasalazine, prednisone, azathioprine, mercaptopurine, methotrexate, or a surgical resection.

15. The method according to claim 11, wherein the statistical algorithm is $\log[p/(1-p)]=-2.140+1.045$ $(\log_{10}REG3\alpha)+0.667$ $(\log_{10}CRP)$ and the combined REG3α/CRP index score is the probability (p) obtained from said statistical algorithm.

16. The method according to claim 11, wherein the optimal classification threshold is selected from 0.35, 0.36, 0.37, 0.38, 0.39, 0.40, 0.41, 0.42, 0.43 and 0.44.

17. The method according to claim 11, wherein the optimal classification threshold is about 0.39.

* * * * *